US00PP16911P2

(12) United States Plant Patent
Klemm

(10) Patent No.: US PP16,911 P2
(45) Date of Patent: Aug. 1, 2006

(54) POINSETTIA PLANT NAMED 'NPCW04095'

(50) Latin Name: ***Euphorbia pulcherrima* Willd.**
Varietal Denomination: NPCW04095

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 13 days.

(21) Appl. No.: 11/141,564

(22) Filed: May 31, 2005

(51) Int. Cl.
*A01H 5/00* (2006.01)

(52) U.S. Cl. ..... Plt./307
(58) Field of Classification Search ..... Plt./307
See application file for complete search history.

*Primary Examiner*—Kent Bell
(74) *Attorney, Agent, or Firm*—C. A. Whealy

(57) ABSTRACT

A new and distinct cultivar of Poinsettia plant named 'NPCW04095', characterized by its uniform and upright plant habit; strong stems; dark green-colored leaves; red-colored flower bracts; large and numerous cyathia; early flowering habit; and good post-production longevity.

1 Drawing Sheet

Botanical denomination: *Euphorbia pulcherrima* Willd.
Cultivar designation: 'NPCW04095'.

BACKGROUND OF THE INVENTION

The present Invention relates to a new and distinct cultivar of Poinsettia plant, botanically known as *Euphorbia pulcherrima* Willd., and hereinafter referred to by the cultivar name 'NPCW04095'.

The new Poinsettia is a product of a planned breeding program conducted by the Inventor in Stuttgart, Germany. The objective of the breeding program is to create new freely branching Poinsettia cultivars with upright and uniform plant habit, attractive flower bract shape and coloration and good postproduction longevity.

The new Poinsettia originated from a cross-pollination made by the Inventor in 1999 of a proprietary selection of *Euphorbia pulcherrima* Willd. identified as code number P 313, not patented, as the female, or seed, parent, with a proprietary selection of *Euphorbia pulcherrima* Willd. identified as code number P 111, not patented, as the male, or pollen, parent. The cultivar NPCW04095 was discovered and selected by the Inventor in 2001 as a flowering plant within the progeny of the stated cross-pollination in a controlled environment in Stuttgart, Germany. The selection of this plant was based on its attractive leaf and flower bract coloration and uniform plant habit.

Asexual reproduction of the new Poinsettia by vegetative terminal cuttings in a controlled environment in Stuttgart, Germany since 2002, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'NPCW04095'. These characteristics in combination distinguish 'NPCW04095' as a new and distinct Poinsettia cultivar:

1. Upright and uniform plant habit.
2. Strong stems.
3. Dark green-colored leaves.

4. Red-colored flower bracts.
5. Large and numerous cyathia.
6. Early flowering habit; response time, about 7.5 weeks.
7. Good post-production longevity.

Plants of the new Poinsettia differ from plants of the female parent selection in the following characteristics:

1. Plants of the new Poinsettia have darker green-colored leaves than plants of the female parent selection.
2. Plants of the new Poinsettia and the female parent selection differ in flower bract coloration as plants of the female parent selection have orange red-colored flower bracts.

Plants of the new Poinsettia differ from plants of the male parent selection in the following characteristics:

1. Plants of the new Poinsettia are more compact than and not as vigorous as plants of the male parent selection.
2. Plants of the new Poinsettia have broader flower bracts than plants of the male parent selection.

Plants of the new Poinsettia can be compared to plants of the cultivar Duepre, disclosed in U.S. Plant Pat. No. 13,644. In side-by-side comparisons conducted in Stuttgart, Germany, plants of the new Poinsettia differed from plants of the cultivar Duepre in the following characteristics:

1. Plants of the new Poinsettia were larger and more vigorous than plants of the cultivar Duepre.
2. Flower bract color of plants of the new Poinsettia resisted fading better than flower bract color of plants of the cultivar Duepre.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a top perspective view of a single flowering plant of 'NPCW04095' grown in a container.

DETAILED BOTANICAL DESCRIPTION

Plants of the new Poinsettia have not been observed under all possible environmental conditions. The phenotype may vary somewhat with variations in environment such as temperature, daylength and light intensity, without, however, any variance in genotype.

The aforementioned photograph, following observations and measurements describe plants grown in Stuttgart, Germany during the fall under commercial practice in a glass-covered greenhouse with day temperatures ranging from 17 to 28° C., night temperatures ranging from 15 to 22° C., and a maximum light level of about 60 kilolux. Cuttings were planted into 13-cm containers when rooted and pinched once. Plants were flowered under natural season short day/long night conditions. Plants were about 17 weeks from unrooted cuttings when the photograph and the detailed botanical description were taken. In the following description, color references are made to The Royal Horticultural Society Colour Chart, 1995 Edition, except where general terms of ordinary dictionary significance are used.

Botanical classification: *Euphorbia pulcherrima* Willd. cultivar NPCW04095.

Parentage:

*Female, or seed, parent.*—Proprietary selection of *Euphorbia pulcherrima* Willd. identified as code number P 313, not patented.

*Male, or pollen, parent.*—Proprietary selection of *Euphorbia pulcherrima* Willd. identified as code number P 111, not patented.

Propagation:

*Type cutting.*—Vegetative terminal cuttings.

*Time to initiate roots.*—Summer: About 12 days at 22° C. Winter: About 15 days at 22° C.

*Time to produce a rooted cutting.*—Summer: About 20 days at 22° C. Winter: About 23 days at 22° C.

*Root description.*—Fibrous; freely-branching; white in color.

Plant description:

*Growth habit.*—Upright and uniform plant habit; inverted triangle; top of plant rounded; moderately vigorous.

*Plant height.*—About 25 to 30 cm.

*Plant diameter or spread.*—About 30 to 45 cm.

*Lateral branch description.*—Quantity per plant: About five to seven lateral branches develop after pinching. Length: About 20 cm. Diameter: About 5 to 10 mm. Internode length: About 2 to 5 cm. Texture: Smooth, glabrous. Strength: Very strong; stems resist breakage. Color: 143A overlain with 183A.

*Foliage description.*—Arrangement: Alternate, single. Quantity of leaves: About 8 to 15 per lateral branch. Length: About 4 to 12 cm. Width: About 3 to 8 cm. Shape: Ovate. Apex: Acute. Base: Obtuse. Margin: Entire or irregularly and slightly lobed. Venation pattern: Pinnate; reticulate. Texture, upper and lower surfaces: Glabrous, smooth. Color: Developing foliage, upper surface: 144B. Developing foliage, lower surface: 143C. Fully expanded foliage, upper surface: 137B. Fully expanded foliage, lower surface: 138B. Venation, upper and lower surfaces: 138B. Petiole: Length: About 3 to 5 cm. Diameter: About 2 to 3 mm. Texture, upper and lower surfaces: Glabrous, smooth. Color, upper and lower surfaces: 183B.

Inflorescence description:

*Inflorescence type and habit.*—Inflorescences are compound corymbs of cyathia with colored flower bracts subtending the cyathia. Inflorescences not persistent.

*Fragrance.*—None detected.

*Natural flowering season.*—Autumn/winter; flower initiation and development is induced under short day/long night conditions.

*Response time.*—Early flowering, about 7.5 weeks.

*Post-production longevity.*—Plants of the new Poinsettia maintain good substance and bract color for about three to four weeks under interior conditions and about four to five weeks under greenhouse conditions.

*Quantity of inflorescences.*—One per lateral branch; about five to seven per plant.

*Inflorescence size.*—Diameter: About 15 to 20 cm. Height (depth): About 2 to 5 cm.

*Flower bracts.*—Quantity of fully developed flower bracts: About six to eight per inflorescence. Length: About 6 to 9 cm. Width: About 4 to 7 cm. Shape: Ovate. Apex: Acute. Base: Obtuse. Margin: Entire with occasional lobing. Texture, upper and lower surfaces: Glabrous, smooth. Color: Developing and fully expanded bracts, upper surface: 45A. Developing and fully expanded bracts, lower surface: 45A. Venation, upper and lower surfaces: Same as lamina. Bract petiole: Length: About 1 to 3 cm. Diameter: About 2 mm. Texture, upper and lower surfaces: Glabrous, smooth. Color, upper and lower surfaces: 187B.

*Cyathia.*—Quantity of cyathia: About five to ten per corymb. Diameter of cyathia cluster: About 1.5 to 2.5 cm. Length: About 4 to 7 mm. Diameter: About 3 to 5 mm. Shape: Ovate. Color, immature and mature: 143C.

*Nectaries.*—Quantity of nectaries: One per cyathium. Diameter: About 2 to 3 mm. Color, immature: 13A to 14B. Color, mature: 24A.

*Peduncle.*—Length: About 1 to 2 mm. Diameter: About 1 mm. Aspect: Erect. Strength: Moderately strong. Texture: Glabrous, smooth. Color: 145A.

*Reproductive organs.*—Stamens: Quantity of stamens: About five to ten per cyathium. Anther shape: Ovate. Anther length: About 1 mm. Anther color: 9A to 12A. Amount of pollen: Moderate. Pollen color: 9A to 12A. Pistils: Quantity of pistils: One per cyathium. Pistil length: About 3 to 5 mm. Style length: About 2 to 3 mm. Stigma shape: Bi-parted. Stigma color: 185A.

Disease/pest resistance: Resistance to pathogens and pests common to Poinsettias has not been observed on plants grown under commercial conditions.

Temperature tolerance: Plants of the new Poinsettia have been observed to tolerate temperatures from 14 to 38° C.

It is claimed:

1. A new and distinct cultivar of Poinsettia plant named 'NPCW04095', as illustrated and described.

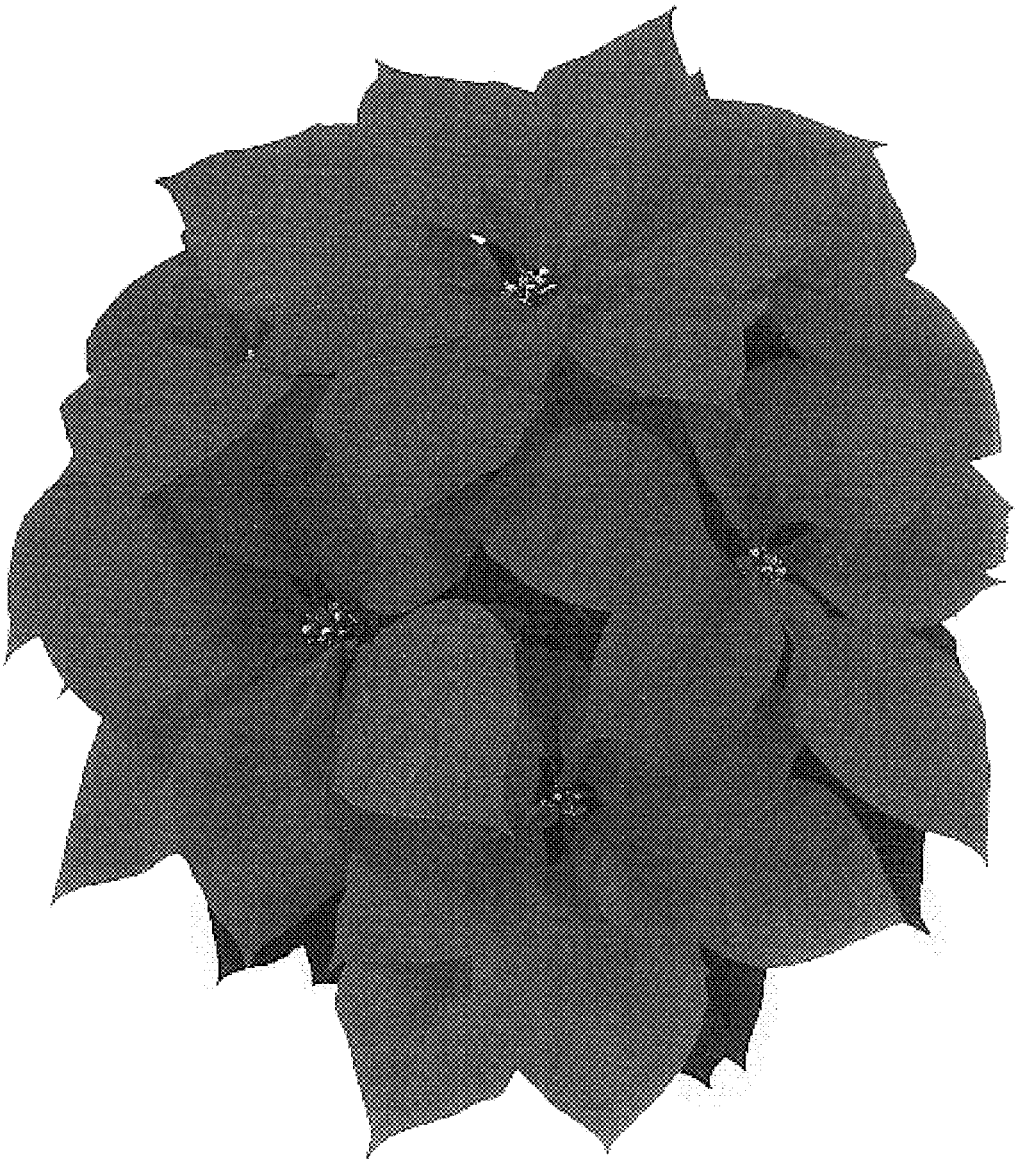

* * * * *